United States Patent
Philippe et al.

(10) Patent No.: US 6,630,004 B1
(45) Date of Patent: *Oct. 7, 2003

(54) OXIDATION DYE COMPOSITION FOR KERATINOUS FIBERS

(75) Inventors: Michel Philippe, Wissous (FR); Thierry Bordier, Tremblay en France (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/167,556

(22) Filed: Oct. 8, 1998

(30) Foreign Application Priority Data

Oct. 8, 1997 (FR) .............................. 97 12555

(51) Int. Cl.$^7$ .................. A61K 7/13; C07C 211/00; C07D 213/72

(52) U.S. Cl. .................. 8/409; 8/423; 8/406; 8/410; 8/416; 546/307; 564/305

(58) Field of Search .................. 8/405, 406, 409, 8/410, 412, 416, 421, 423, 565–579, 594, 597, 649; 564/305, 443; 546/297, 307; 540/527, 531

(56) References Cited

U.S. PATENT DOCUMENTS

| | | | |
|---|---|---|---|
| 3,532,743 A | 10/1970 | Kalopisis et al. | 562/437 |
| 3,931,912 A | 1/1976 | Hsiung | 222/94 |
| 4,136,079 A | 1/1979 | Katayama et al. | 260/37 |
| 4,150,230 A | * 4/1979 | Mislin et al. | 544/356 |
| 5,041,608 A | * 8/1991 | Mano et al. | 560/43 |

FOREIGN PATENT DOCUMENTS

| | | |
|---|---|---|
| DE | 2 852 252 | 9/1980 |
| FR | 1 506 081 | 12/1967 |
| FR | 2220257 | 10/1974 |
| GB | 1 227 395 | 4/1971 |
| JP | 49-125395 | 11/1974 |
| JP | 62-11850 | 1/1987 |
| JP | 2-68546 | 3/1990 |
| JP | 6-503583 | 4/1994 |
| WO | WO 96/19476 | 6/1996 |

OTHER PUBLICATIONS

Caplus Abstract of Srivastava et al, "Azo Dyes. I. Preparation of N–2–methyl–4–(phenylazo)phenylglycines,"Indian J. Appl. Chem. 1969, (No month available).*
English Language Derwent Abstract of DE 2 852 252, 9/80.
English Language Derwent Abstract of GB 1 227 395, 4/71.
English Languaage Derwent Abstract of JP 2–68546, 3/90.
Patent Abstracts of Japan, Abstract of JP6032769, 2/94.

Ernst D. Bergmann et al., "A New AMino Acid Reagent, 2,4–Dinitro–5–fluoroaniline", Journal of Organic Chemistry, vol. 26, 1961, pp. 1480–1483.
Juana Cabanes et al., "Chemical and enzymatic oxidation of 4–methylcatechol in the presence and absence of L–serine, Spectrophotometric determination of intermediates", Biochim. Biolhys, ACTA, 1987, pp. 190–196.
Muriel Doise et al., "Synthesis of Functionalized N–(2–Pyridyl)–αAmino Acids and Esters by Ring Opening of Imidazo[1,2–a]pyridine", Heterocycles, vol. 34, No. 11, 1992, pp. 2079–2093.
N. Yu. Sokolova et al., "Acridine Derivatives Modified by Benzimidazole Fragments", Russian Journal of Organic Chemistry, vol. 29, No. 7, 1993, pp. 1211–1217.
Charles C. Irving et al., "Protein Binding of Model Quinone Imides. III. Preparation of Nε–(1–Hydroxy–2–acetamido–4–fluorenyl)–DL–lysine", Journal of Organic Chemistry, Vol 26, 1961, pp. 1869–1861.
Peter S. Marfey et al., "Reaction of Bovine Pancreatic Ribonuclease A with 1,5–Difluoro–2, 4–dinitrobenzene", The Journal of Biological Chemistry, vol. 240, No. 8, 1965, pp. 3264–3269.
Charles Zviak, Science des Traitements Capillaires, published by Masson, 1988, p. 278.
Chemical Abstracts Registry (120256–15–7) no date available.
G. Sun et al., "Synthesis of Chiral, 1–(2'–Amino–2'–carboxyethyl)–1,4–dihydro–6,7–quinoxaline–2,3–diones: α–Amino–3hydroxy–5–methyl–4–isoxazolepropionate Receptor Agonists and Antagonists," J. Med. Chem., vol. 39, No. 22, 1996, pp. 4430–4438.
Linda Benson et al., "Short Communications, Membrane Preconcentration–Capillary Electrophoresis–Mass Spectrometry (mPC–CE–MS) Analysis of 3–Phenylamino–1, 2–Propanediol (PAP) Metabolites," J. High Resol. Chromatogr., vol. 19, No. 8, 1996, pp. 291–294.
M. Sado et al., "Kinetics and Mechanisms of the Complex Formation Reaction of Aluminium ((III) with 7–(2–Carboxyethyl)Amino–8–Hydroxy–5–Quinolinesulphonic Acid and Related Ligands: Evidence for pH–Dependent Linkage Isomerism," Polyhedron, vol. 13, No. 1, 1996, pp. 103–114.

(List continued on next page.)

Primary Examiner—Margaret Einsmann
(74) Attorney, Agent, or Firm—Finnegan, Henderson, Farabow, Garrett & Dunner, LLP

(57) ABSTRACT

An oxidation dyeing composition for keratinous fibers, in particular hair, comprising, as oxidation base, at least one compound of the formula:

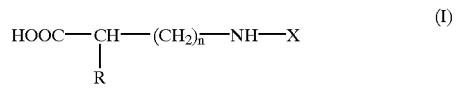

(I)

$$\text{HOOC}-\underset{R}{\text{CH}}-(\text{CH}_2)_n-\text{NH}-\text{X}$$

where n=0–11, R represents H, amino, a saturated or unsaturated, linear or branched $C_1$–$C_6$ alkyl or is a radical chosen from radicals defined in the specification.

3 Claims, No Drawings

OTHER PUBLICATIONS

A. Patel et al., "Novel Inhibitors of Enkephalin–Degrading Enzymes II: 4–Carboxymethylamino–4–Oxo–3(Phenylamino) Butanoic Acids as Enkephalinase Inhibitors," J. Enzyme Inhibition, vol. 5, No. 5, 1991, pp. 133–149.

Rodriguez et al., Chemical Abstracts, vol. 101, No. 15, Abstract No. 2130101y, p. 660, Oct. 8, 1984.

Mascagna et al., Chemical Abstracts, vol. 118, No. 21, Abstract No. 212564s, p. 864, May 24, 1993.

D. Maysinger et al., "Free–Wilson Analysis of Quinoline Derivatives," Pharm. Acta Helv., vol. 56, No. 6, 1981, pp. 151–154.

E. Szarvasi et al., "[4H]Dihydro–5,6 (s)–triazolo–[4,3–a] benzodiazepines–,5 à activité analgésique et anti–inflammatoire," Eur. J. Med. Chem.—Chimica Therapeutica, vol. 13, No. 2, 1978, pp. 113–119.

S. Katayama et al., "Carboxylate and Sulfonate Polyaddition Polymers," Int. Prog. Urethanes, 1981, pp. 15–32.

V. Yu. Mitskyavichyus et al., "Synthesis adn Cyclization of N–(2–Hydroxyphenyl)–and N–(2–Benzyloxphenyl)–β–alanines," Chemistry of Heterocyclic Compounds, (English language translation of Khimiya Geterotsiklicheskikh Soedinenii) vol. 27, No. 4, 1991, pp. 527–531.

R. S. Baltrushis et al., "Synthesis and Transformations of 1–(4–Hydroxyphenyl)Dihydrouracils," Chemistry of Heterocyclic Compounds, (English language translation of Khimiya Geterotsiklicheskikh Soedinenii) vol. 18, No. 10, 1982, pp. 1400–1406.

* cited by examiner

OXIDATION DYE COMPOSITION FOR KERATINOUS FIBERS

The present invention relates to a composition for dyeing keratinous fibers, in particular human keratinous fibers, comprising, as oxidation base, at least one compound of formula (I), defined below, which can be referred to, for convenience sake only, as an amino acid derivative substituted on an amino group by a group with an aromatic nucleus, to a dyeing process using such a composition and employing development by an oxidizing agent and to compounds of formula (I'), defined below, which can also be referred to, for convenience sake only, as amino acid derivatives in which an amino group is substituted by a group with an aromatic nucleus.

It is known to dye keratinous fibers, in particular human hair, with dyeing compositions comprising oxidation dye precursors comprising "oxidation bases", in particular ortho- or para-phenylenediamines and ortho- or para-aminophenols, as well as couplers, also known as coloring modifiers, more particularly aromatic meta-phenylenediamines, meta-aminophenols and meta-diphenols, which make it possible to modify and to enrich with highlights the "base" colorations obtained with the condensation products of oxidation bases.

In the field of oxidation hair dyeing, it is essential to have available oxidation dye precursors having a high dyeing power, in order to allow the formulator to create a broad palette of shades. Furthermore, it is also important for the oxidation dye precursors to have a high dyeing power at neutral pH in the region of 7 rather than at basic pH (pH≧9), in order not to damage the keratinous fiber and to reduce irritation to the scalp.

It is as a result of much research that the inventors have discovered that it is possible to obtain intense natural shades on keratinous fibers, in particular at a pH in the region of neutrality, by using, as oxidation bases, compounds of the formula (I) set forth below which can also be characterized as amino acid derivatives substituted on an amino group by a group with an aromatic nucleus.

The subject-matter of the present invention is thus an oxidation dyeing composition for keratinous fibers, in particular for human keratinous fibers, such as hair, comprising, in a medium appropriate for dyeing, as oxidation base, at least one compound having the formula (I):

$$\text{HOOC}-\underset{\underset{R}{|}}{\text{CH}}-(\text{CH}_2)_n-\text{NH}-\text{X} \tag{I}$$

in which:

n is an integer ranging from 0 to 11;
R represents a hydrogen atom, an amino radical, a saturated or unsaturated, linear or branched, $C_1$–$C_6$ alkyl radical or a radical chosen from:

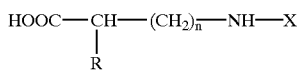

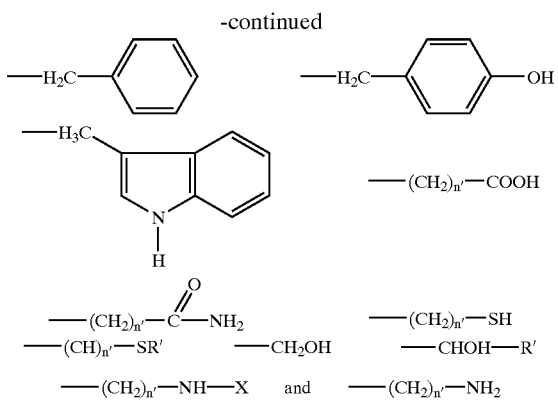

R' represents a saturated or unsaturated, linear or branched, $C_1$–$C_6$ alkyl radical;
n' is an integer ranging from 1 to 6;
X represents an aromatic group with one or two rings, wherein said ring or rings may comprise at least one heteroatom chosen from S, N or O; and further wherein said ring or rings are substituted, wherein at least one substituent on said ring or rings is an —NHR" group or an —OH radical in the para or ortho position on the aromatic group X with respect to the —NH— group, wherein R" denotes a hydrogen atom or an optionally hydroxylated, saturated or unsaturated, linear or branched, $C_1$–$C_6$ alkyl radical,
or an acid addition salt thereof,
with the proviso that compounds in which n=0, R=H and X is a 4-hydroxyphenyl radical are not included within formula (I).

The compounds of the formula (I) can be optically active isomers or mixtures of such isomers.

The novel dyes thus obtained make it possible to obtain strong and non-toxic natural colorings at neutral pH in the region of 7.

These novel dyes, in addition, exhibit good resistance to light, washing, bad weather, perspiration and the various treatments to which hair may be subjected.

Another subject of the invention is the ready-for-use dyeing composition comprising at least one compound of formula (I) as defined above, as oxidation base, and at least one oxidizing agent.

The invention is also targeted at a process for dyeing keratinous fibers, in particular human keratinous fibers, such as hair, which involves applying, to these fibers, at least one composition (A) comprising, in a medium appropriate for dyeing, as oxidation base, at least one compound of formula (I) as defined above and in developing the color in alkaline, neutral or acidic medium using an oxidizing agent which is added only at the time of use to the composition (A) or which is present in a composition (B) applied simultaneously or sequentially in a separate fashion.

Another subject of the invention is multi-compartment dyeing devices or kits, the first compartment of which comprises a composition (A) comprising at least one compound of formula (I) as defined above as oxidation base and the second compartment of which comprises a composition (B) comprising an oxidizing agent in a medium appropriate for dyeing.

A glycine derivative, namely N-(4-aminophenyl)glycine, is known in thermography as transfer reagent in a duplication process disclosed in French Patent FR-A-1,506,081 and in photography according to Patent GB-A-1,227,395 or Patent Application JP-A-02068546.

Another subject of the present invention is compounds of formula (I'):

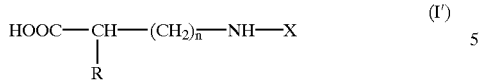

in which:
n is an integer ranging from 0 to 11;
R represents a hydrogen atom, an amino radical, a saturated or unsaturated, linear or branched, $C_1$–$C_6$ alkyl radical or a radical chosen from:

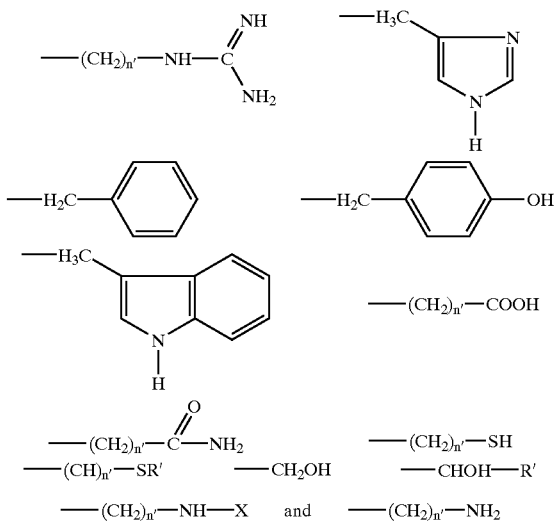

R' represents a saturated or unsaturated, linear or branched, $C_1$–$C_6$ alkyl radical;
n' is an integer ranging from 1 to 6;
X represents an aromatic group with one or two rings, wherein said ring or rings may comprise at least one heteroatom chosen from S, N and O; and said ring or rings are substituted, wherein at least one substituent on said ring or rings is an —NHR" group or an —OH radical in the para or ortho position on the aromatic group X with respect to the —NH— group, wherein R" denotes a hydrogen atom or an optionally hydroxylated, saturated or unsaturated, linear or branched, $C_1$–$C_6$ alkyl radical, with the proviso that said ring or rings are not substituted by any nitro groups,
or an acid addition salt thereof
with the further proviso that compounds in which
n=0, R=H and X is a 4-aminophenyl, 4-hydroxyphenyl, 3-hydroxy-2-pyridyl or 4-hydroxy-3-pyridyl radical;
n=0, R=–$CH_3$ and X is a 3-hydroxy-2-pyridyl radical; and
n=0, R=–$CH_2OH$ and X is a 3,4-dihydroxy-6-methylphenyl radical
are not included within formula (I').

These compounds of the formula (I') can be optically active isomers or mixtures of such isomers.

In the formula (I) or (I'), X preferably represents a phenyl or pyridyl ring substituted by an amino group —$NH_2$.
The preferred compounds of the formula (I') are:
Nε-(4-aminophenyl)-L-lysine;
Nε-(4-amino-2-pyridyl)-L-lysine;
Nα-(4-aminophenyl)-L-lysine;
Nα,Nε-di(4-aminophenyl)-L-lysine;
N-(4-aminophenyl)-L-serine;
6-[N-(4-aminophenyl)amino]caproic acid;
α-N-(4-aminophenyl)amino-ε-caprolactam; and
their acid addition salts.

The acid addition salts are preferably chosen from hydrochlorides, sulphates, hydrobromides and tartrates.

The preferred compounds of the formula (I) for being used in oxidation dyeing according to the invention are: Nε-(4-aminophenyl)-L-lysine, Nε-(4-amino-2-pyridyl)-L-lysine, N-(4-aminophenyl)glycine, Nα-(4-aminophenyl)-L-lysine, Nα,Nε-di(4-aminophenyl)-L-lysine, N-(4-aminophenyl)-L-serine, 6-[N-(4-aminophenyl)amino] caproic acid, α-N-(4-aminophenyl)amino-ε-caprolactam, and their acid addition salts.

The compounds of formula (I) or (I') are prepared according to the following procedures, depending on whether they are lysine derivatives, glycine derivatives or other derivatives, such as w-amino acids and lactam derivatives.

LYSINE DERIVATIVES

Preparation of Aromatic Nitro Derivatives at the Nε Position of Lysine

General Procedure:

10 g (54.75 mmol) of L-lysine monohydrochloride are dissolved in 44 ml (2 eq) of a 10% aqueous sodium hydroxide solution and 120 ml of water in a 500 ml three-necked flask equipped with a thermometer and a 50 ml dropping funnel. A solution of 6.8 g (0.5 eq) of copper sulphate pentahydrate in 40 ml of water is introduced into the reaction mixture, followed by 4.6 g (1 eq) of sodium hydrogencarbonate and 40 ml of ethanol. A solution containing 1 equivalent of 4-fluoronitrobenzene or of 2-chloro-5-nitropyridine in 40 ml of ethanol is prepared and then run dropwise onto the homogeneous mixture. After heating for 6 hours at reflux, the reaction mixture is cooled and then filtered. The green-yellow precipitate, corresponding to the final product in the form of a copper complex, is washed with water and with acetone and then dried in an oven under vacuum. To remove the copper, x mol of complex are treated with 2 eq of thioacetamide at reflux of water. After having removed the copper sulphide by filtration on paper, the filtrate is cooled in order to obtain, by crystallization, the expected final product.

EXAMPLE 1

Nε-(4-Nitrophenyl)-L-lysine

According to the procedure described above, 4.1 g of a yellow product are obtained from 4-fluoronitrobenzene, i.e. a yield of 46%.

Analyses:
M.p.: 254°–258° C. (Kofler bench)
Elemental analysis ($C_{12}H_{17}N_3O_4$, MW = 267.287)

|  | C | H | N | O |
|---|---|---|---|---|
| % calc. | 53.92 | 6.41 | 15.72 | 23.94 |
| % found | 53.64 | 6.36 | 15.85 | 24.16 |

EXAMPLE 2

Nε-(4-Nitro-2-pyridyl)-L-lysine

According to the procedure described above, 10.7 g of a yellow product are obtained from 2-chloro-5-nitropyridine, i.e. a yield of 73%.

Analyses:
M.p.: >260° C. (Kofler bench)
Elemental analysis ($C_{11}H_{16}N_4O_4$, MW = 268.275)

|  | C | H | N | O |
|---|---|---|---|---|
| % calc. | 49.25 | 6.01 | 20.88 | 23.86 |
| % found | 48.96 | 6.09 | 20.95 | 24.10 |

Reduction of the Para-nitro Derivatives of Nε-Lysine

EXAMPLE 3

Synthesis of Nε-(4-Aminophenyl)-L-lysine Trihydrochloride 2 g (7.48 mmol) of Nε-(4-nitrophenyl)-L-lysine are dissolved in 30 ml of ethanol, 9 ml of water and 5.2 ml (3.5 eq) of 5N hydrochloric acid in a 250 ml glass reactor (Paar apparatus). 2 g of palladium-on-charcoal with a moisture content of 50% and an active content of 10% are then introduced. The mixture is hydrogenated under a pressure of approximately $2.76 \times 10^5$ Pa for 1 hour and at a temperature of 10° C. After filtering through celite, the filtrate is evaporated. The purplish oily residue is taken up in ethanol and precipitated from a large volume of acetone with stirring. After filtration, 2.6 g of a white crystalline powder are obtained, i.e. a final yield of 99%.

Analyses:
M.p.: 146–150° C. (Kofler bench)
Elemental analysis ($C_{12}H_{19}N_3O_2.3HCl$, MW = 346.687)

|  | C | H | N | O | Cl |
|---|---|---|---|---|---|
| % calc. | 41.57 | 6.40 | 12.12 | 9.23 | 30.68 |
| % found | 41.04 | 6.55 | 11.78 | 10.57 | 30.28 |

EXAMPLE 4

Synthesis of Nε-(4-Amino-2-pyridyl)-L-lysine Trihydrochloride 4 g (14.9 mmol) of Nε-(4-nitro-2-pyridyl)-L-lysine are suspended in 80 ml of ethanol and 8 ml of water in a 100 ml three-necked flask equipped with a thermometer and a reflux condenser. 6 g of palladium-on-charcoal (10% active and 50% moisture) are then introduced, followed by 40 ml of cyclohexene. The mixture is brought to reflux for 2 hours and is then cooled, before being filtered through celite. After having run 60 ml (4 eq) of 1N hydrochloric acid onto the filtrate, the latter is evaporated to dryness and the residue is taken up in ethanol and precipitated from acetone. After filtration, 3.4 g of product are obtained, i.e. a final yield of 66%.

Analyses:
M.p.: 180–185° C. (Kofler bench)
Elemental analysis ($C_{11}H_{18}N_4O_2.3HCl$, MW = 347.675)

|  | C | H | N | O | Cl |
|---|---|---|---|---|---|
| % calc. | 38.00 | 6.09 | 16.11 | 9.2 | 30.59 |
| % found | 38.03 | 6.05 | 15.97 | 9.55 | 30.43 |

Preparation of Aromatic Nitro Derivatives at the Nα Position of Lysine

EXAMPLE 5

Synthesis of Nα-(4-Nitrophenyl)-Nε-(benzyloxycarbonyl)-L-lysine 5 g (17.83 mmol) of Nε-benzyloxycarbonyl-L-lysine are dissolved in 130 ml of water in the presence of 0.71 g (1 eq) of sodium hydroxide and 2.25 g (1.5 eq) of sodium bicarbonate in a 250 ml three-necked flask equipped with a reflux condenser and a thermometer. A solution of 2.85 ml (1.5 eq) of 4-fluoronitrobenzene in 70 ml of ethanol is run into the reaction mixture, which is subsequently brought to reflux for 48 hours. The mixture is neutralized with 1N hydrochloric acid, evaporated and then extracted with ethyl acetate. The aqueous phase is acidified to pH~3 and again extracted with ethyl acetate. The organic phases are combined, washed with water and dried over sodium sulphate. After evaporation, an orangy-yellow oil is obtained, which oil is purified by flash chromatography (eluent: $CH_2Cl_2$ 95/$CH_3OH$ 5) to give 1.6 g of a yellow crystalline product, i.e. a final yield of 22%.

Analyses:

M.p.: 136°–140° C. (Kofler bench); HPTLC (Merck silica): eluent ethyl acetate 80/methanol 20; $R_f$=0.30 (UV visualization).

The NMR spectra are recorded on a 500 MHz Bruker AMX and are in accordance with the expected structure.

Reduction of the Para-nitro Derivatives of Nα-Lysine

EXAMPLE 6

Synthesis of Nα-(4-Aminophenyl)-L-lysine Trihydrochloride 0.40 g (1 mmol) of Nα-(4-nitrophenyl)-Nε-(benzyloxycarbonyl)-L-lysine is dissolved in 20 ml of ethanol, 5 ml of water and 0.5 ml (3.5 eq) of 5N hydrochloric acid in a 250 ml glass reactor (Paar apparatus). 0.5 g of palladium-on-charcoal (50% moisture and 10% active) is then introduced. The mixture is hydrogenated under a pressure of approximately $2.76 \times 10^5$ Pa for 45 minutes and at a temperature of 12° C. After filtration through celite, the filtrate is evaporated. The purplish oily residue is taken up in ethanol and precipitated from a large volume of acetone with stirring. After filtration, 0.3 g of a white crystalline powder is obtained, i.e. a final yield of 93%.

| Elemental analysis ($C_{12}H_{19}N_3O_2.3HCl.2H_2O$, MW = 382.7) | | | | | |
|---|---|---|---|---|---|
| | C | H | N | O | Cl |
| % calc. | 37.62 | 6.27 | 10.97 | 16.72 | 27.82 |
| % found | 37.00 | 6.63 | 10.35 | 15.28 | 27.44 |

Preparation of Aromatic Nitro Derivatives at the Nα and Nε Positions of Lysine

EXAMPLE 7

Synthesis of Nα,Nε-di(4-Nitrophenyl)-L-lysine 5 g (34.2 mmol) of L-lysine are dissolved in 100 ml of water in the presence of 1.4 g (1 eq) of sodium hydroxide and 8.6 g (3 eq) of sodium bicarbonate in a 250 ml three-necked flask equipped with a reflux condenser and a thermometer. A solution of 10.8 ml (3 eq) of 4-fluoronitrobenzene in 60 ml of ethanol is run into the mixture, which is brought to reflux (85°–90° C.) for 5 days. The cooled mixture is extracted with ethyl ether. The aqueous phase is acidified to pH~3 with 5N hydrochloric acid. A gummy precipitate is formed, which precipitate is extracted with dichloromethane in the presence of a small amount of methanol. The organic phase is washed with water to neutrality, dried over sodium sulphate and then evaporated to give an orange-colored oil which crystallizes in the presence of ethyl ether. 11.7 g of a yellow crystalline product are obtained, i.e. a yield of 88%.

Analyses:
M.p.: 72°–76° C. (Kofler bench)

| Elemental analysis ($C_{18}H_{20}N_4O_6$, MW = 388.38) | | | | |
|---|---|---|---|---|
| | C | H | N | O |
| % calc. | 55.67 | 5.19 | 14.43 | 24.72 |
| % found | 55.90 | 5.13 | 14.79 | 24.96 |

Reduction of the Para-nitro Derivatives of Nα- and Nε-Lysine

EXAMPLE 8

Synthesis of Nα,Nε-di(4-Aminophenyl)-L-lysine Tetrahydrochloride 1.5 g (3.86 mmol) of Nα,Nε-di(4-nitrophenyl)-L-lysine are dissolved in 35 ml of ethanol, 7 ml of water and 3.5 ml (3.5 eq) of 5N hydrochloric acid in a 250 ml glass reactor (Paar apparatus). 3 g of palladium-on-charcoal (50% moisture and 10% active) are then introduced. The mixture is hydrogenated under a pressure of approximately $2.76 \times 10^5$ Pa for 1 hour and at a temperature of 10° C. After filtering through celite, the filtrate is evaporated. The purplish oily residue is taken up in ethanol and precipitated from a large volume of acetone with stirring. After filtration, 0.8 g of a white crystalline powder is obtained, i.e. a final yield of 44%.

Analyses:
HPTLC (Merck silica): eluent $NH_4OH$ 6/$CH_3OH$ 47/$CH_2Cl_2$ 47; $R_f$=0.75 (UV and ninhydrin visualization).
The NMR spectra are recorded on a 400 MHz Bruker AMX and are in accordance with the expected structure.

GLYCINE DERIVATIVES

Preparation of Aromatic Nitro Derivatives of Glycine

EXAMPLE 9

Synthesis of N-(4-Nitrophenyl)glycine 7.5 g (0.1 mol) of glycine are dissolved in 100 ml of water in the presence of 4 g (1 eq) of sodium hydroxide and 8.4 g (1 eq) of sodium bicarbonate in a 250 ml three-necked flask equipped with a reflux condenser and a thermometer. A solution of 14.1 g (1 eq) of 4-fluoronitrobenzene in 60 ml of ethanol is run into the mixture, which is brought to reflux (85°–90° C.) for 5 hours. The mixture is cooled and then extracted 3 times with ethyl acetate. The aqueous phase is acidified to pH~3 with 5N hydrochloric acid. A yellow precipitate is formed; the mixture is left overnight in a refrigerator. The product is pulled dry and rinsed with acetone. 10.8 g of a yellow crystalline product are obtained. The filtrates are concentrated to a quarter of their initial volume. A yellow precipitate appears and is isolated by filtration. 7.3 g are obtained, i.e. a total weight of 18.1 g (yield of 83%).

Analyses:
HPTLC (Merck silica): eluent $NH_4OH$ 1/$CH_3OH$ 4/$CH_2Cl_2$ 15; $R_f$=0.4 ($UV_{254\ nm}$ and ninhydrin visualization).

Reduction of the Aromatic Nitro Derivatives of Glycine

EXAMPLE 10

Synthesis of N-(4-Aminophenyl)glycine.2HCl 1 g (5 mmol) of (4-nitrophenyl)glycine is dissolved in 20 ml of ethanol, 5 ml of water and 2.5 ml (2.5 eq) of 5N hydrochloric acid in a 250 ml glass reactor (Paar apparatus). 1 g of palladium-on-charcoal (50% moisture and 10% active) is then introduced. The mixture is hydrogenated under a pressure of approximately $2.76 \times 10^5$ Pa for 1 hour 30 minutes at a temperature of 20° C. After filtering through celite, the filtrate is evaporated to dryness. A white solid is obtained which is taken up in 50 ml of acetone, filtered and dried under vacuum at 40° C. 0.95 g of a white powder is obtained.

| Elemental analysis ($C_8H_{10}N_2O_2.2HCl$, MW = 239.103) | | | | | |
|---|---|---|---|---|---|
| | C | H | N | O | Cl |
| % calc. | 40.19 | 5.06 | 11.72 | 13.38 | 29.66 |
| % found | 39.85 | 5.52 | 11.19 | 14.97 | 28.71 |

OTHER DERIVATIVES

ω-AMINO ACIDS

EXAMPLE 11

Synthesis of 6-[N-(4-Nitrophenyl)amino]caproic Acid 5 g (38.11 mmol) of 6-aminocaproic acid are dissolved in 50 ml of water in the presence of 1.5 g (1 eq) of sodium hydroxide and 4.2 g (1.3 eq) of sodium bicarbonate in a 250 ml three-necked flask equipped with a reflux condenser and a thermometer. A solution of 4.9 ml (1.2 eq) of 4-fluoronitrobenzene in 50 ml of ethanol is run into the mixture, which mixture is subsequently brought to reflux (85°–90° C.) for 48 hours. The mixture is cooled and then extracted 3 times with dichloromethane. The aqueous phase is acidified to pH~3 with 5N hydrochloric acid. A yellow precipitate is formed; the mixture is left overnight in a refrigerator. The precipitate is pulled dry and washed with water and with acetone. After drying, 9.3 g of a yellow product are obtained, i.e. a final yield of 97%.

Analyses:
M.p.: 160°–162° C. (Kofler bench)
Elemental analysis ($C_{12}H_{16}N_2O_4$, MW = 252.272)

|  | C | H | N | O |
|---|---|---|---|---|
| % calc. | 57.13 | 6.39 | 11.1 | 25.37 |
| % found | 56.86 | 6.38 | 10.99 | 25.51 |

EXAMPLE 12

Synthesis of 6-[N-(4-Aminophenyl)amino]caproic Acid Dihydrochloride 2 g (7.9 mmol) of 6-[N-(4-nitrophenyl)amino]caproic acid are partially dissolved in 40 ml of ethanol and 2 ml of water in a 150 ml three-necked flask equipped with a thermometer and a reflux condenser. 2 g of palladium-on-charcoal (10% active and 50% moisture) are then introduced, followed by 20 ml of cyclohexene. The mixture is brought to reflux for 2 hours and is then cooled, before being filtered through celite. After having run 4 ml (2.5 eq) of 5N hydrochloric acid onto the filtrate, the latter is evaporated to dryness and the residue is taken up in ethanol and precipitated from acetone. After filtration, 1.9 g of a white product are obtained, i.e. a final yield of 81%.

Elemental analysis ($C_{12}H_{18}N_2O_2.2HCl$, MW = 295.211)

|  | C | H | N | O | Cl |
|---|---|---|---|---|---|
| % calc. | 48.82 | 6.83 | 9.49 | 10.84 | 24.02 |
| % found | 48.43 | 6.79 | 9.43 | 11.55 | 23.17 |

LACTAM DERIVATIVES

EXAMPLE 13

Synthesis of α-N-(4-Nitrophenyl)amino-ε-caprolactam 5 g (39 mmol) of α-amino-ε-caprolactam are dissolved in 50 ml of dimethylformamide and 5.5 ml (1 eq) of triethylamine in a 100 ml three-necked flask equipped with a reflux condenser and a thermometer. 4.1 ml (1.5 eq) of 4-fluoronitrobenzene are then run into the reaction mixture, which is subsequently brought to a temperature of 70° C. for 48 hours. The mixture is cooled and is then precipitated from water. An orangy-yellow precipitate is isolated by filtration and is then purified on a silica column (eluent: dichloromethane 95/methanol 5). 2.7 g of a yellow product are obtained, i.e. a final yield of 28%.

Analyses:
M.p.: 216–218° C. (Kofler bench)
Elemental analysis ($C_{12}H_{15}N_3O_3$, MW = 249.272)

|  | C | H | N | O |
|---|---|---|---|---|
| % calc. | 52.82 | 6.07 | 16.86 | 19.26 |
| % found | 56.97 | 6.15 | 16.54 | 19.07 |

EXAMPLE 14

Synthesis of α-N-(4-Aminophenyl)amino-ε-caprolactam Dihydrochloride 2 g (8 mmol) of α-N-(4-nitrophenyl)amino-ε-caprolactam are partially dissolved in 40 ml of 95° ethanol in a 150 ml three-necked flask equipped with a thermometer and a reflux condenser. 2 g of palladium-on-charcoal (10% active and 50% moisture) are then introduced, followed by 20 ml of cyclohexene. The mixture is brought to reflux for 3 hours and is then cooled, before being filtered through celite. After having run approximately 6 ml (~3.5 eq) of 5N hydrochloric acid onto the filtrate, the latter is evaporated to dryness and the residue is taken up in ethanol and precipitated from acetone. After filtration, 1.9 g of a white product are obtained, i.e. a final yield of 81%.

Elemental analysis ($C_{12}H_{17}N_3O.2HCl.H_2O$, MW = 310.2)

|  | C | H | N | O | Cl |
|---|---|---|---|---|---|
| % calc. | 46.42 | 6.77 | 13.54 | 10.31 | 22.88 |
| % found | 47.25 | 6.82 | 13.75 | 10.96 | 22.35 |

The oxidation dyeing compositions according to the invention generally comprise approximately 0.01 to 10% by weight, preferably approximately 0.05 to 5% by weight, of at least one oxidation base of formula (I) defined above.

The oxidizing agent is preferably chosen from hydrogen peroxide, urea hydrogen peroxide, alkali metal bromates, or persalts, such as perborates and persulphates and enzymes such as peroxidases and oxidoreductases with two electrons. The use of hydrogen peroxide is particularly preferred.

The composition (A), which includes the oxidation base of formula (I) as described above, can have a pH preferably ranging from 3 to 12, more preferably ranging from 5 to 11, which can be adjusted to the chosen value either by means of basifying agents commonly used in the dyeing of keratinous fibers, such as ammonia, alkaline carbonates, alkanolamines, for example mono-, di- and triethanolamines and their derivatives, sodium hydroxide, potassium hydroxide or the compounds of formula:

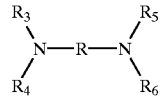

in which R is a propylene residue optionally substituted by a hydroxyl group or a $C_1$–$C_4$ alkyl radical; and $R_3$, $R_4$, $R_5$ and $R_6$, simultaneously or independently of one another, represent a hydrogen atom, a $C_1$–$C_4$ alkyl radical or a $C_1$–$C_4$ hydroxyalkyl radical, or by means of conventional acidifying agents, such as inorganic or organic acids, such as, for example, hydrochloric, tartaric, citric and phosphoric acids.

The pH of the composition (B) including the oxidizing agent as defined above is such that, after mixing with the composition (A), the pH of the composition applied to human keratinous fibers varies, preferably ranging from 3 to 12, more preferably ranging from 5 to 11. It is adjusted to the desired value using acidifying or optionally basifying agents well known in the state of the art, such as those described above.

The oxidizing composition (B) is preferably composed of an aqueous hydrogen peroxide solution.

According to a preferred embodiment of the dyeing process of the invention, the dyeing composition (A) described above is mixed, at the time of use, with an oxidizing solution in an amount sufficient to develop a coloring. The mixture obtained is subsequently applied to human keratinous fibers and left in contact for 5 to 40 minutes, preferably 15 to 30 minutes, after which the hair is rinsed, washed with a shampoo, rinsed again and dried.

The dyeing compositions according to the invention can comprise, in addition to the oxidation dye precursors of formula (I) defined above, other oxidation dye precursors chosen from para-phenylenediamines, bisphenylalkylenediamines, para-aminophenols, ortho-aminophenols, heterocyclic bases, benzene couplers and heterocyclic couplers.

Preference is very particularly given, among para-phenylenediamines, to para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and their acid addition salts.

Preference is given, among bisphenylalkylenediamines, to N,N'-bis(β-hydroxyethyl)-N,N'-bis(4'-aminophenyl)-1,3-diaminopropanol or one of its acid addition salts.

Mention may more particularly be made, among para-aminophenols, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol, 4-amino-2-fluorophenol and their acid addition salts.

Mention may more particularly be made, among ortho-aminophenols, of 2-aminophenol, 2-amino-5-methylphenol, 2-amino-6-methylphenol, 5-acetamido-2-aminophenol and their acid addition salts.

Mention may more particularly be made, among heterocyclic bases, of pyridine derivatives, pyrimidine derivatives, pyrazole derivatives, pyrazolopyrimidine derivatives and their acid addition salts.

Mention may more particularly be made, among benzene couplers, of meta-aminophenol, 2-methyl-5-aminophenol, 2-methyl-5-[N-(β-hydroxyethyl)amino]phenol, 2-methoxy-5-aminophenol, 2-(β-hydroxyethyloxy)-5-aminophenol, 5-[N-(β-hydroxyethyl)amino]-4-methoxy-2-methylphenol, 5-amino-4-methoxy-2-methylphenol, 5-amino-4-chloro-2-methylphenol, 5-amino-2,4-dimethoxyphenol, 5-[N-(γ-hydroxypropyl)amino]-2-methylphenol, 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 2,4-diaminophenoxyethanol, 1-(β-aminoethyloxy)-2,4-diaminobenzene, 2-amino-1-(β-hydroxyethyloxy)-4-(methylamino)benzene, 1,3-diamino-4,6-bis(β-hydroxyethyloxy)benzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2-amino-4-[N-(β-hydroxyethyl)amino]anisole, resorcinol and their acid addition salts.

Mention may be made, among heterocyclic couplers, of indole derivatives, benzomorpholine derivatives, indoline derivatives, benzimidazole derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives and thiazoloazole S-oxide and thiazoloazole S,S-dioxide derivatives.

The dyeing compositions according to the invention can also comprise direct dyes chosen from azo or anthraquinone dyes and nitro derivatives of the benzene series and/or melanin precursors, in particular for modifying the shades or enriching them with highlights.

The dyeing compositions can also comprise antioxidizing agents. These can be chosen in particular from sodium sulphite, thioglycolic acid, thiolactic acid, sodium bisulphite, dehydroascorbic acid, hydroquinone, 2-methylhydroquinone, tert-butylhydroquinone, 3-methyl-1-phenyl-5-pyrazolone and homogentisic acid and are then generally present in proportions ranging from approximately 0.05 to approximately 1.5% by weight with respect to the total weight of the composition.

The dyeing compositions also comprise, in their preferred embodiment, surface-active agents well-known in the art in proportions ranging from approximately 0.5 to approximately 55% by weight, more preferably ranging from 2 to 50% by weight, with respect to the total weight of the composition, organic solvents in proportions ranging from approximately 1 to approximately 40% by weight, in particular ranging from 5 to 30% by weight, with respect to the total weight of the composition or any other cosmetically acceptable adjuvant known in the prior art in hair oxidation dyeing.

The composition applied to hair can be provided in various forms, such as in the liquid, cream or gel form or in any other form appropriate for carrying out dyeing of keratinous fibers and in particular of human hair. In particular, it can be packaged under pressure in an aerosol container in the presence of a propellant and can form a foam.

Concrete examples illustrating the invention will now be given.

DYEING EXAMPLES

Dyeing Examples 1 to 10 in Neutral Medium

The following dyeing compositions were prepared (contents in grams):

|  | EXAMPLE | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Nε-(4-Aminophenyl)-L-lysine trihydrochloride (Oxidation base in accordance with the invention) | 1.038 | 1.038 | 1.038 | 1.038 | 1.038 | — | — | — | — | — |
| N-(4-Aminophenyl)glycine dihydrochloride (Oxidation base in accordance with the invention) | — | — | — | — | — | 0.717 | 0.717 | 0.717 | 0.717 | 0.717 |
| para-Aminophenol (Additional oxidation base) | — | — | 0.327 | — | — | — | — | 0.327 | — | — |
| 2-Methyl-5-[N-(β-hydroxyethyl)amino]phenol (Coupler) | — | 0.543 | — | — | — | — | 0.543 | — | — | — |
| Resorcin (Coupler) | — | — | — | 0.33 | — | — | — | — | 0.33 | — |
| meta-Aminophenol (Coupler) | — | — | — | — | 0.327 | — | — | — | — | 0.327 |
| Common dyeing vehicle | (*) | (*) | (*) | (*) | (*) | (*) | (*) | (*) | (*) | (*) |
| Demineralized water, q.s. for | 100 g | 100 g | 100 g | 100 g | 100 g | 100 g | 100 g | 100 g | 100 g | 100 g |

The dyes were used in an equal molar amount, namely $3 \times 10^{-3}$ mol %.

| (*) Common dyeing vehicle: | |
| --- | --- |
| 96° Ethanol | 18 g |
| Pentasodium salt of diethylenetriamine-pentaacetic acid, sold under the name Masquol DTPA by the company Protex | 1.1 g |
| Sodium metabisulphite as an aqueous solution containing 35% A.M. | 0.68 g A.M. |
| K$_2$HPO$_4$/KH$_2$PO$_4$ (1.5 M/1 M) | 10 g |

At the time of use, each of the above dyeing compositions was mixed, weight for weight, with a 20-volume hydrogen peroxide solution (6% by weight).

The mixture obtained was applied for 30 minutes to locks of natural grey hair containing 90% of white hairs, at the rate of 30 g per 3 g of hair. The locks were subsequently rinsed, washed with a standard shampoo, rinsed again and then dried.

The hair coloring was evaluated visually and then measured with a Minolta CM 2002 calorimeter.

The shades obtained appear in the table below:

| EXAMPLE | Tone | Shade on natural hair |
| --- | --- | --- |
| 1 | 6 | Mat ashy dark blond |
| 2 | 6 | Ashy dark-purple dark blond |
| 3 | 6 | Golden natural dark blond |

-continued

| EXAMPLE | Tone | Shade on natural hair |
| --- | --- | --- |
| 4 | 6 | Grey dark blond |
| 5 | 6 | Green dark blond |
| 6 | 6 | Slightly purplish grey dark blond |
| 7 | 6 | Irisated dark-purple dark blond |
| 8 | 5 | Ashy natural light chestnut |
| 9 | 7.5 | Golden beige light blond |
| 10 | 5 | Grey green light chestnut |

Dyeing Examples 11 to 20 in Basic Medium

The following dyeing compositions were prepared (contents in grams):

|  | EXAMPLE | | | | | | | | | |
| --- | --- | --- | --- | --- | --- | --- | --- | --- | --- | --- |
|  | 11 | 12 | 13 | 14 | 15 | 16 | 17 | 18 | 19 | 20 |
| Nε-(4-Aminophenyl)-L-lysine trihydrochloride (Oxidation base in accordance with the invention) | 1.038 | 1.038 | 1.038 | 1.038 | 1.038 | — | — | — | — | — |
| N-(4-Aminophenyl)glycine dihydrochloride (Oxidation base in accordance with the invention) | — | — | — | — | — | 0.717 | 0.717 | 0.717 | 0.717 | 0.717 |
| para-Aminophenol (Additional oxidation base) | — | — | 0.327 | — | — | — | — | 0.327 | — | — |
| 2-Methyl-5-[N-(β-hydroxyethyl)amino]phenol (Coupler) | — | 0.543 | — | — | — | — | 0.543 | — | — | — |
| Resorcin (Coupler) | — | — | — | 0.33 | — | — | — | — | 0.33 | — |
| meta-Aminophenol (Coupler) | — | — | — | — | 0.327 | — | — | — | — | 0.327 |
| Common dyeing vehicle | (*) | (*) | (*) | (*) | (*) | (*) | (*) | (*) | (*) | (*) |
| Demineralized water, q.s. for | 100 g | 100 g | 100 g | 100 g | 100 g | 100 g | 100 g | 100 g | 100 g | 100 g |

The dyes were used in an equal molar amount, namely $3 \times 10^{-3}$ mol %.

| (*) Common dyeing vehicle: | |
| --- | --- |
| 96° Ethanol | 18 g |
| Pentasodium salt of diethylenetriamine-pentaacetic acid, sold under the name Masquol DTPA by the company Protex | 1.1 g |
| Sodium metabisulphite as an aqueous solution containing 35% A.M. | 0.68 g A.M. |
| 20% Aqueous ammonia | 10 g |

The method of application of the dyes was identical to that used in Examples 1 to 10.

The hair coloring was evaluated in the same way.

The shades obtained appear in the table below:

| EXAMPLE | Tone | Shade on natural hair |
|---|---|---|
| 11 | 8 | Grey green light blond |
| 12 | 7 | Dark-purple blond |
| 13 | 7.5 | Mat golden blond |
| 14 | 7.5 | Beige grey light blond |
| 15 | 6.5 | Bluish grey blond |
| 16 | 8.5 | Light blond with yellow green highlights |
| 17 | 8 | Dark-purple light blond |
| 18 | 6.5 | Mat golden blond |
| 19 | 8.5 | Light blond with yellow green highlights |
| 20 | 7.5 | Blond with grey highlights |

The levels of "tone" mentioned in the above tables are based on the classification of natural shades below, one tone separating each shade from that which immediately follows or precedes it (see "Science des Traitements Capillaires" [Science of Hair Care] by C. Zviak, published by Masson, 1988, p. 278).

This classification is as follows:

1) Black
2) Brown
3) Dark chestnut
4) Chestnut
5) Light chestnut — 2 tones
6) Dark blond — 4 tones
7) Blond — 6 tones
8) Light blond
9) Very light blond
10) Light light blond On comparing Examples 1 to 5, carried out in neutral medium, with Examples 11 to 15, carried out in basic medium with the same oxidation base, namely Nϵ-(4-aminophenyl)-L-lysine, it is seen that the latter is stronger in neutral medium than in basic medium, because the levels of tone obtained in basic medium are higher by 0.5 to 2 tones, that is to say lighter, than those obtained in neutral medium with the same dye precursors.

Likewise, if Examples 6 to 10 are compared with Examples 16 to 20 in which N-(4-aminophenyl)glycine is used, it is observed that the dyeings obtained in basic medium have levels of tone higher by 1 to 2.5 tones, that is to say are lighter, than those obtained in neutral medium with the same oxidation dye precursors.

We claim:

1. A ready-to-use oxidation dyeing composition for keratinous fibers comprising, in a medium appropriate for dyeing:

at least one oxidizing agent chosen from hydrogen peroxide, urea hydrogen peroxide, alkali metal bromates, persalts and enzymes, as oxidation base, at least one compound chosen from Nϵ-(4-aminophenyl)-L-lysine, Nϵ-(4-amino-2-pyridyl)-L-lysine, N-(4-aminophenyl)glycine, Nα-(4-aminophenyl)-L-lysine, Nα,Nϵ-di(4-aminophenyl)-L-lysine, N-(4-aminophenyl)-L-serine, 6-(N-(4-aminophenyl)amino)caproic acid, and the acid addition salts of any of the foregoing.

2. A compound, wherein said compound is α-N-(4-aminophenyl)amino-ϵ-caprolactam, or an acid addition salt thereof.

3. An oxidation dyeing composition for keratinous fibers comprising, in a medium suitable for dyeing, as oxidation base, α-N-(4-aminophenyl)amino-ϵ-caprolactam, or an acid addition salt thereof.

* * * * *